(12) United States Patent
Hsieh et al.

(10) Patent No.: US 7,727,471 B2
(45) Date of Patent: Jun. 1, 2010

(54) RARE CELL DETECTION USING FLAT-PANEL IMAGER AND CHEMILUMINESCENT OR RADIOISOTOPIC TAGS

(75) Inventors: Huangpin Ben Hsieh, Mountain View, CA (US); JengPeng Lu, San Jose, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 514 days.

(21) Appl. No.: 10/937,009

(22) Filed: Sep. 9, 2004

(65) Prior Publication Data

US 2006/0051816 A1   Mar. 9, 2006

(51) Int. Cl.
*G01N 15/06* (2006.01)
(52) U.S. Cl. ............ 422/68.1; 436/518; 436/527; 435/283.1; 435/287.1; 435/288.7; 422/50; 422/82.05; 422/82.08
(58) Field of Classification Search .......... 436/518, 436/527; 435/283.1, 287.1, 288.7; 422/50, 422/68.1, 82.05, 82.08
See application file for complete search history.

(56) References Cited

U.S. PATENT DOCUMENTS

| 5,142,147 | A | * | 8/1992 | Kawamata et al. ........ 250/310 |
| 5,759,774 | A | | 6/1998 | Hackett et al. |
| 5,764,792 | A | | 6/1998 | Kennealy |
| 5,932,872 | A | * | 8/1999 | Price ........ 250/201.3 |
| 5,993,634 | A | | 11/1999 | Simpson et al. |
| 6,272,207 | B1 | | 8/2001 | Tang |
| 6,303,323 | B1 | | 10/2001 | Laskey et al. |
| 6,410,300 | B1 | | 6/2002 | Sammulski et al. |
| 7,079,257 | B1 | * | 7/2006 | Kirkpatrick et al. ........ 356/502 |
| 2001/0036640 | A1 | * | 11/2001 | D'Amico ........ 435/7.1 |
| 2002/0012420 | A1 | | 1/2002 | Bani-Hashemi et al. |
| 2002/0160443 | A1 | | 10/2002 | Tsipouras et al. |
| 2002/0168657 | A1 | | 11/2002 | Chen et al. |
| 2003/0007601 | A1 | * | 1/2003 | Jaffray et al. ........ 378/65 |
| 2003/0012420 | A1 | | 1/2003 | Verwoerd et al. |
| 2003/0108949 | A1 | * | 6/2003 | Bao et al. ........ 435/7.1 |
| 2003/0170613 | A1 | * | 9/2003 | Straus ........ 435/5 |
| 2004/0058401 | A1 | | 3/2004 | Bossy et al. |
| 2004/0184678 | A1 | * | 9/2004 | Maddison ........ 382/291 |

OTHER PUBLICATIONS

Radbruch et al., "Detection and Isolation of Rate Cells," *Curr. Opin. Immunol.*, 7:270-273 (1995).
Hochtlen-Vollmar et al., "Occult epithelial tumor cells detected in bone marrow by . . . ," Int. J. Cancer: 70, 396-400, (1997) .

(Continued)

*Primary Examiner*—Melanie Yu
(74) *Attorney, Agent, or Firm*—Fay Sharpe LLP

(57) ABSTRACT

Disclosed is a system using a large area flat panel imager which is specifically adapted for rare cell detection methods. The system generally includes an imager having a sample receiving surface which can provide a digital or electronic image of a sample deposited on the surface. The system also includes a selectively positionable microscope and/or camera which are used to obtain high resolution images of the deposited samples. An electronic controller can also be used in conjunction with the imager, microscope, and/or camera to selectively position at least one of those components to focus on desired regions of the deposited sample. The noted system is particularly adapted for use with chemiluminescence or other tagging technologies.

23 Claims, 5 Drawing Sheets

OTHER PUBLICATIONS

Bajaj et al., "Ultra-Rare-Event Detection Performance of a Custom Scanning . . . ," Cytometry, 39: 285-294, (2000).

Rahn et al., "Achieving High-Resolution in flat-Panel Imagers for Digital Radiography," Proceedings of SPIE Vo. 3770, 136-145, (1999).

Weisfield et al., Proceedings of SPIE 4320, 209 (2001).

Musiani et al., "Sensitive Chemiluminescence in Situ Hybridization for . . . ," The Journal of Histochemistry & Cytochemistry, 45(5): 729-735, (1997).

Street et al, "Comparative Study of $PBI_2$ and . . . ," Proceedings of SPIE, vol. 4320, 1-11, (2001).

Weisfield et al., "Electronic noise analysis of a 127-micron pixel . . . ," Proceedings of SPIE, vol. 4320 209-218, (2001).

Doherty, "PIN Diode Fundamentals," MicroNote Series 701, No date.

Specification of Microarray Analyzer, Applied Biosystems, at www.appliedbiosystems.com, 4 pages, (2003).

Oosterwijk et al., "Strategies for Rare-Event Detection: An Approach for . . . ," Am. J. Hum. Genet. vol. 63, 1783-1792, (1998).

\* cited by examiner

RARE CELL DETECTION USING FLAT-PANEL IMAGER AND CHEMILUMINESCENT OR RADIOISOTOPIC TAGS

BACKGROUND

The present exemplary embodiment relates to cell screening techniques. It finds particular application in conjunction with cell screening methods and related instrumentation, and will be described with particular reference thereto. However, it is to be appreciated that the present exemplary embodiment is also amenable to other like applications.

Many medical applications would benefit from the ability to detect rare cell events. For example, it is known that fetal cells circulate in the maternal blood stream. See Oosterwijk et.al., *Am. J. Hum. Genet.*, 63: 1783-1792 (1998); Bajaj et. al., *Cytometry*, 39: 285-294 (2000), the contents of which are incorporated by reference herein. Cancer cells can be found circulating in the bloodstream depending on the stage of cancer. See Hochten-Wollmar et. al., *Int. J. Cancer*, 70: 396-400 (1997), the contents of which are incorporated by reference herein. Shed tissues of people infected with viruses can also be detected in the circulation system at an early stage. See Musiani et. al., *J. Histochem. Cytochem.*, 45(5): 729-735 (1997), the contents of which are incorporated by reference herein. Early detection of these rare cells would allow invasive diagnostic procedures such as amniocentesis to be avoided, cancer development to be properly monitored and treatment to be prescribed, or viral outbreak to be prevented. Detection of these rare cells would also find use in other diagnostic or research applications.

To provide statistically significant information, it is necessary to screen about 50-100 million blood cells in order to detect rare cell events occurring at scales of 1 in 1 to 10 millions. Therefore, a system that could efficiently and quickly process a large number of cells, such as up to 100 million, at a time would be beneficial. However, these numbers are exemplary and should not be construed as limiting.

Measuring emitted light has become a widely used method in detecting rare cell events. Two methods may be used to create these emitted photons. Chemiluminescence (CL) refers to the light emitted by a chemical reaction, especially when the chemical reaction is catalyzed by an enzyme. For example, luciferase catalyzes the oxidation of luciferin and produces green light. Alkaline phosphatase can be used with 1,2-dioxetane substrates such as CSPD and CDP-Star to produce light as well. In one method, the enzyme is linked to an antibody specific to a protein marker and the antibody binds the protein. Reagents are introduced which are cleaved by the enzyme and cause CL. A second analytical technique known as fluorescence uses a molecule (usually an organic dye or fluorchrome but more recently inorganic semiconductor nanocrystal material such as quantum dot is also used as a tagging molecule) which absorbs light at one wavelength and emits light at a different wavelength. The molecule is first bound to a cell or cell component such as a protein, lipid, chromosome, or other such components. A light (usually a laser) is then used at the wavelength absorbed by the molecule to excite it and the amount of light emitted at the emission wavelength is measured. These assays are useful because the amount of light emitted is proportional to, and thus can be used to determine the number of cells or cell components to which the molecule is bound that is present in the sample. Similarly, the rate of light output can also be used to determine the concentration of the cells or cell components present in the sample. These assays are very sensitive, have a wide dynamic range within which they can be used, and have low background noise. The kinetics of CL also allow for two different types of kinetics. In "flash" kinetics, light output peaks rapidly, then dies off quickly. In "glow" kinetics, light output is steady for a comparatively long period of time. Because of these characteristics, they are widely used in studying gene expression and regulation within living cells as well as for protein/nucleic acid blots.

Cell detection based on illumination to generate fluorescence is currently used in two main categories: flow cytometry and, image cytometry, which includes conventional or digital microscopy as well as laser scanning microscopy. In flow cytometry, cells are suspended in solution and travel one by one past a sensing point. Fluorescent compounds can be attached to the cells or cell components and detected using a laser which excites the compound and causes it to fluoresce. In conventional fluorescent microscopy, cells are fixed on a slide and stained with a fluorescent compound, then viewed under a microscope. Broad spectrum light sources (such as mercury arc lamp or Xenon flash lamp) coupled with specific excitation/emission filters are used to block undesired excitation lights and allow detection of weaker fluorescence. They usually include automatic stage movement and use low-magnification scanning to identify potential cells of interest followed by high magnification to reject false positives. Bajaj described one such setup of a fluorescent microscope. It's also noted that laser can be used to excite these fluorescent compounds in a system called laser scanning cytometer (LSC). Both of these image-based cytometry methods direct the excitation light and collect the fluorescence through a microscope objective.

However, both flow cytometry and fluorescent microscopy have several problems which hinder their use in clinical applications. Bajaj et al. concluded that flow cytometry could be used to screen cells quickly, but generated high numbers of false positives due to autofluorescence, nonspecific staining, and cell aggregates. See also Radbruch et. al., *Curr. Opin. Immunol.* 7:270-273 (1995), the contents of which are incorporated by reference herein. Also, in practice a high number of cells bunch or clump together, making it impossible to examine each cell separately. The cells being examined cannot be saved for confirmation of the diagnosis, nor can the high-resolution images needed for such confirmation be taken by current instrumentation.

Conventional fluorescent microscopy or laser scanning cytometry are unsuitable for clinical use because it usually requires at least 10-20 microscope slides and from 5 to 30 hours to scan 100 million blood cells. In addition, the use of fluorescence creates the need to filter strong exciting light and also leads to the possibility of bleaching, both of which affect the sensitivity of the assay. However, microscopy allows the cells to be saved for confirmation or for images to be captured either digitally or on film. Finally, the equipment costs of both techniques are very high.

A significant cause of delay in imaging is related to the process by which cells or samples are examined. In current image cytometry systems, the cell samples are usually processed in two steps. First, the imaging device (e.g., a microscope with a CCD camera) is used at low resolution and passes over the entire area of the slide in order to detect all "potential hits." However, with a typical field of view of only a few square millimeters through a low-magnification 4× objective and a CCD camera, moving the objective across entire surfaces of multiple slides is a very time-consuming bottleneck. After this "pre-screening," the imaging device then reexamines the "potential hits" at high resolution (such as 20× or 40×) by making a second pass over the slide. This second pass increases the amount of time required for a complete examination of the cell samples.

There is therefore a need for methods and systems which are less expensive, have higher throughput of cells, and allow for confirmation of results. The present exemplary embodiment contemplates a new and improved approach for rare cell detection methods and systems which overcome the above-referenced problems and others.

BRIEF DESCRIPTION

In accordance with one aspect of the present exemplary embodiment, a system is provided for qualitatively and quantitatively detecting cells. The system comprises a large area imager having an image forming surface. The imager is able to form digital or electronic images of a sample without the help of intermediate image forming lenses. The system also comprises a selectively positionable microscope-camera assembly in viewing relation with the image forming surface. The camera is adapted to acquire an image through the microscope in the form of digital data. The system additionally comprises an electronic controller in communication with the imager, microscope, and camera. The electronic controller is configured to position the imager and microscope-camera relative to each other in order to image selected regions of the image forming surface.

The exemplary embodiment provides a system that is less expensive and has higher throughput than present systems. The exemplary embodiment also provides a technique for confirmation of the results. Furthermore, the exemplary embodiment is also reusable.

In accordance with another aspect of the present exemplary embodiment, a method is provided for detecting the presence of tagged biological agents in a sample. The method comprises a step of providing a system having an imager, a microscope, a camera, and a sample receiving surface. The method also comprises a step of providing a sample containing a biological agent to be detected. The method comprises a step of tagging the biological agent to be detected within the sample. The method also comprises a step of depositing the sample upon the sample receiving surface. The method further comprises a step of obtaining a digital image of the deposited tagged sample from the system. The method additionally comprises a step of analyzing the digital image and selecting one or more regions of the tagged sample for high resolution examination. The method also comprises a step of positioning the imager and microscope-camera relative to each other so the microscope can image a selected region of the tagged sample determined in the analyzing step. The method also comprises a step of obtaining a second digital image of the selected region of the tagged sample. And, the method comprises a step of confirming the detection of the tagged biological agent. The method also comprises a step to ensure a darkened image exposure environment, such as by placing the imaging area in a dark box or by placing the entire system in a dark room.

The exemplary embodiment reduces delay in processing time by using a flat-panel imager to pre-screen the cell samples, which is much faster compared to current methods. The flat-panel imager can image the entire area of the substrate simultaneously and in parallel. Because the imager directly converts images into digital form, processing time for film is eliminated.

Other advantages and benefits of the present exemplary embodiment will become apparent to those of ordinary skill in the art upon reading and understanding the following detailed description.

BRIEF DESCRIPTION OF THE DRAWINGS

The exemplary embodiment may take form in various components and arrangements of components, and in various steps and arrangements of steps. The drawings are only for purposes of illustrating various aspects and are not to be construed as limiting the exemplary embodiment.

DETAILED DESCRIPTION

Figure 1:
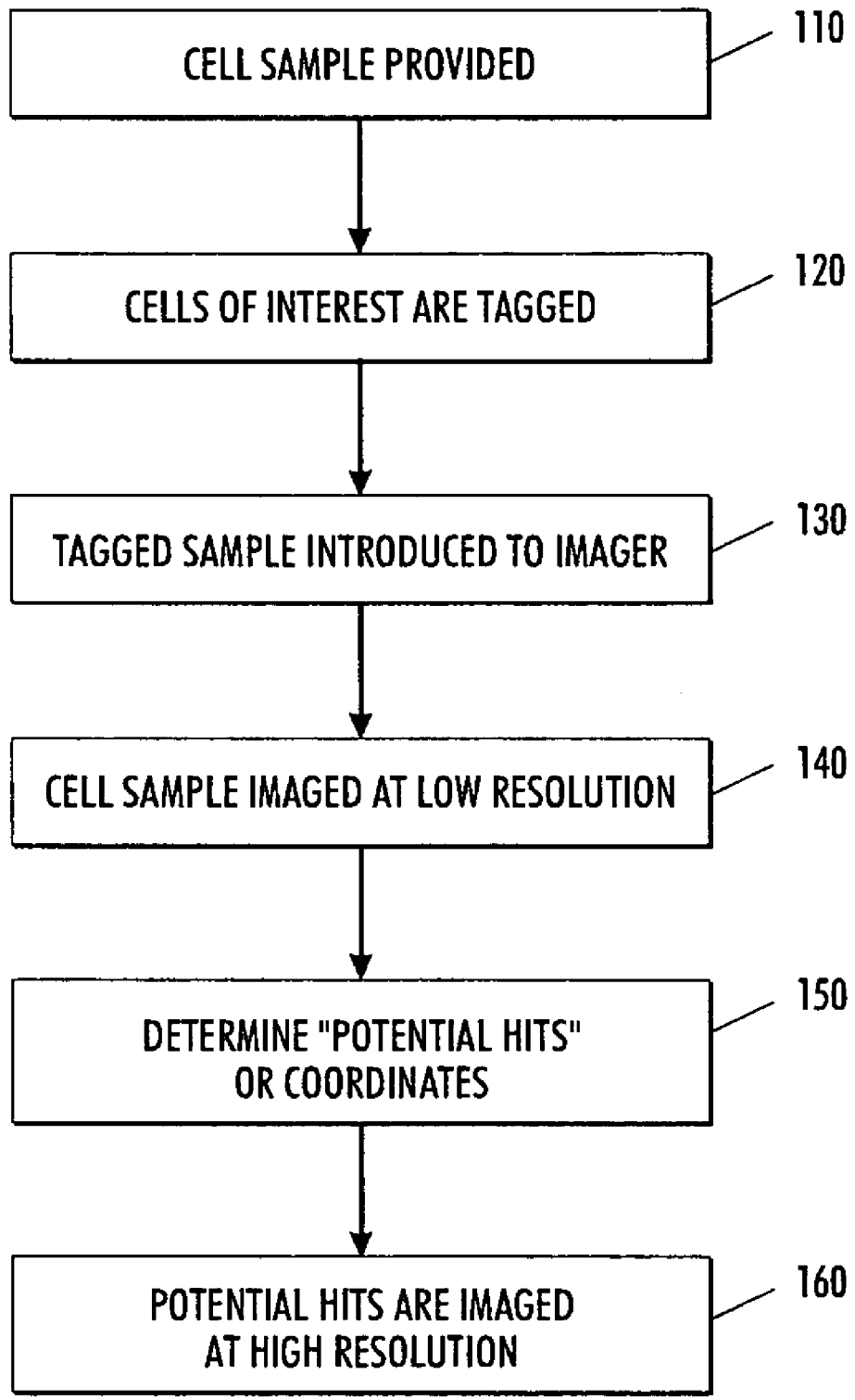
FIG. 1 is a block diagram of a method used to detect rare cells implemented in accordance with the exemplary embodiment.

The exemplary embodiment systems and methods are particularly directed to detecting the presence of tagged biological agents in a sample. The systems and methods are adapted for qualitatively and quantitatively detecting cells, and specifically, rare cells. Although the exemplary embodiment systems and methods are described in terms of rare cell detection, it will be understood that the exemplary embodiment encompasses other systems and methods for detecting, reviewing, analyzing, or sampling biological agents.

The current art in digital imaging systems includes amorphous silicon arrays and large area charge-coupled diode (CCD) devices. Key factors in the performance of such devices include the pixel pitch and the fill factor. In the exemplary embodiment described herein, the pixel pitch refers to the length of one side of a pixel, which is generally square. The pixel pitch determines the number of photons that can be detected and traced to a specific spatial location. The fill factor refers to the percentage of each pixel that can be used to detect the photons. A higher fill factor translates into increased sensitivity because fewer photons fall into the "gaps" in and between pixels where they cannot be detected. A higher fill factor also aids in noise reduction and image resolution by increasing the detected signal. Amorphous silicon arrays can be produced in large sizes, have a pixel pitch of about 100 to 127 μm, and are relatively inexpensive. Large area CCDs have superior image quality because they can have very fine pixel size and a high fill factor, but they are difficult to produce in large sizes and consequently have a high cost. "Linear" CCD arrays are also used in imaging, such as in scanners and copiers, but have moving parts for scanning an area. Moving parts reduce the life expectancy of the device and also increase the difficulty of manufacture.

In one aspect, the exemplary embodiment system uses a large area flat-panel imager to detect and spatially locate rare cells through CL. The term "large area" with reference to a flat panel imager as described herein refers to imagers having an imaging area or an image forming surface of at least about 100 $cm^2$, such as provided by an imaging area of 10 cm by 10 cm. Typically, this refers to imagers having an imaging area of greater than 200 $cm^2$, greater than 400 $cm^2$, greater than 600 $cm^2$, greater than 800 $cm^2$, greater than 1000 $cm^2$, and approximately 1200 $cm^2$. The exemplary embodiment includes the use of imagers having an imaging area greater than 1200 $cm^2$. A flat-panel imager is an imager which uses a detection means, such as photoconductors, in the form of a flat surface. Currently, such imagers are available from companies such as General Electric and Dpix for use in medical imaging, non-destructive testing, security imaging, and research. Several types of imagers are discussed in U.S. Pat. No. 6,272,207, the content of which is incorporated by reference herein. The exemplary embodiment can utilize a flat panel imager that includes a two dimensional array of photosensing devices. In particular, an imager can be comprised of thin film transistors (TFTs) on an amorphous silicon substrate. Rahn et al. discusses these TFTs in *Proc. SPIE,* 3770: 136-145 (1999), the content of which is incorporated by reference herein. TFTs have been demonstrated on a single substrate of dimensions of approximately 30 cm by 40 cm with a pixel pitch of 100 to 127 µm. This pixel pitch size gives good image resolution and allows for a large dynamic range of detection.

A TFT array used in the exemplary embodiment compares well to a CCD array. A typical cell density when spread upon a substrate is 300,000 to 500,000 cells per $cm^2$. With 10 µm diameter cell size, 50 million cells prepared on a 100 $cm^2$ substrate will cover 39% of the surface, assuming a non-overlapping monolayer and no loss of cells during preparation. Actual coverage is likely less as cells may overlap and cell loss is expected. On a flat-panel imager with square pixels with dimensions of 100 µm, the 100 $cm^2$ substrate could be imaged with one million pixels. As target cells are ultra rare, more than one target cell in a pixel (100 µm by 100 µm) might occur, but only at very low frequency. As many as 100 "potential hits" might occur, which could include 50 true positives and 50 false positives. These 100 "potential hits" are further inspected with a high-magnification imaging device (such as a microscope and a sensitive high quantum efficiency CCD camera) to obtain high-resolution images for confirmation. For example, through a 40× objective, a back-thinned back-illuminated CCD camera (e.g. Hamamatsu ORCA II BT 512) having 512 by 512 square pixels with effective pixel size of 12.29 µm can image an area of about 157 µm by 157 µm. Within this image high resolution of a potential positive rare cell and many non-rare cells would provide a good context for positive identification of a true rare cell. The lower resolution of the flat-panel imager due to its 100 µm pixel pitch would not affect the subsequent resolution of the microscope image which is used for confirmation. It is understood that CCD cameras with higher resolution and better sensitivity can be employed if necessary. It may also be possible to use an image intensifier coupled with a sensitive camera for detecting ultra low light in a much shorter time.

In another aspect of the exemplary embodiment, a method is provided for tagging target cells, cell fragments, and cell components such as proteins with a luminescent molecule. In one approach, immunocytostaining method is used to tag the target. In another approach, a nucleic acids-based method similar in principle to fluorescent in situ hybridization (FISH) is used. Unlike immunostaining or FISH, where fluorochromes are conjugated to antibody or probing DNA, in CL detection enzymes capable of cleaving chemical bonds of CL reagents to generate lights are conjugated to the antibody or DNA. CL reagents are then applied onto the sample to allow chemiluminescence to be generated at targeted sites. In yet another approach, radioisotopes are used in place of the CL enzyme to tag the target. Multiple tagging methods (including fluorescence) could also be used simultaneously on one cell sample to more precisely locate target cells. Multiple probes containing different enzymes that react with different CL reagents to generate light of different wavelengths can also be used to target one or more cellular markers. In this case, proper wavelength-specific filters are implemented on the imager to separate these probes.

In accordance with the present exemplary embodiment, a method is provided for qualitatively and quantitatively detecting cells. Cells are spread across a substrate (e.g., a slide). The cells are tagged with antibodies that carry an enzyme that will cause luminescence when suitable reagents are applied. The substrate-sample is then placed on a flat-panel imager that detects the luminescence and pre-screens the cells. Digital processing is used to eliminate some false positives and to provide the spatial data necessary for a high-resolution imaging device, such as a high-power microscope to reexamine the cells in that area for confirmation of the diagnosis. A recording device, such as a CCD camera or a complementary metal oxide semiconductor (CMOS) sensor with associated digital storage medium, also records the high-resolution image for later viewing and/or analysis. Confirmation of the diagnosis can occur through human intervention, automatic identification, or other techniques.

An exemplary embodiment method for detecting rare cells using a flat-panel imager and tagging is given in FIG. 1. A cell sample is provided 110 which contains the desired target rare cells. The cell sample may come from any natural source and be of any type of cell, but the cell sample is typically in the form of a blood sample containing blood components such as plasma, red blood cells, white blood cells, and the like. The cell sample is then processed. Some of the components of blood, e.g., red blood cells, may be removed. If the tagging method requires access to cell components inside the cell, then the cells in the cell sample would need to be fragmented, broken up or permeabilized to allow that access. Other processing may occur which enhances the imaging of the cell sample. The cell sample is then attached to a substrate. Usually, the cell sample is spread as evenly across the substrate as possible. Cells will adhere to the substrate or the adhesion may be promoted with certain "conditionings" on the substrate. These substrate surface conditionings may include a layer or layers of amino acids, collagen, amino silane, etc., just to name a few; or it could be a nylon or nitrocellulose coating to enhance the chemiluminescent signals. The cells and/or cellular components are usually fixed with a fixing agent to allow for handling, preservation, and other reasons. The substrate is usually a slide; however, the slide may be customized to enhance certain properties or have a form which aids in diagnostic processing. Larger substrates (e.g., having the size of a standard wellplate or larger) that can hold one or more patient samples are particularly suitable for this detection method. Slides or other sample receiving surfaces can include one or more coatings that facilitate binding of cells thereto. Generally, such coatings are compatible with CL detection. Tagging agents or probes, e.g. antibody conjugated with CL enzyme, are added to the cell sample 120. After these tagging agents have attached to the target rare cells, several washing steps may be included to reduce or eliminate non-specific binding. CL reagents are then added and spread evenly. The substrate is then placed on the flat-panel imager for imaging 130. The cell sample is analyzed at low resolution 140 and "potential hits" are identified 150. This analysis and identification is usually performed by electronic means such as a computer, but may also be performed using human intervention. The coordinates of these potential hits are recorded relative to certain prescribed calibration marks on the substrate and then these coordinates are translated into stage movements. Next, a high-resolution imaging device is used to reexamine the cells identified as "potential hits" 160 and confirm the diagnosis. This can be done by either moving the stage holding the substrate-imager assembly or by moving the microscope and CCD camera. In this way, detection of tagged rare cells and rejection of false positives are made possible via inspection of the high-resolution images. Again, this confirmation may be performed by electronic means or by human intervention.

An exemplary method for preparing cells to be analyzed on a flat-panel imager, e.g. steps 110-130 depicted in FIG. 1, is as follows:

1) A conventional or custom (large) microscopy slide (substrate) is provided which has a defined "well structure" which has its chemistry optimized for mammalian cell adhesion (such as the Erie CLEARCELL or ADCELL chemistry) inside the well and which is surrounded by a hydrophobic chemistry or coating that will repel the aqueous solution used for cell deposition.

2) Blood samples of patients are processed with $NH_4Cl$ buffer to lyse red blood cells. The samples are then centrifuged, washed with phosphate buffered saline (PBS) to remove erythrocytes and $NH_4Cl$, and re-suspended in PBS. An appropriate amount of sample is pipet-transferred onto the substrate. The solution is spread evenly across the substrate with a blade to form a thin layer. Incubation occurs at 37° C. with high humidity for 40 min followed by an addition of growth medium and further incubation of 20 min to promote cell adhesion.

3) Cells are then fixed by 2% paraformaldehyde for 20 minutes at room temperature followed by 2 rinses for 3 minutes each in PBS.

4) Non-specific binding is blocked by incubation with 20% human AB serum for 20 minutes at 37° C.

5) After tapping off the serum, an appropriate amount of primary antibody diluted in the same serum is added and the substrate is incubated for an hour. An example would be 1:100 dilution for mouse anti-human cytokeratine antibody (Monoclonal anti-Pan Cytokeratin, Sigma catalog # C-2562). After one hour, the antibody solution is rinsed off with PBS.

6) An enzyme-linked secondary antibody (e.g. alkaline phosphatase linked goat anti-mouse IgG) is diluted in AB serum and an appropriate amount is applied into the well. The substrate is incubated for 30 minutes and the antibody solution is then rinsed off twice with PBS.

7) An appropriate amount of chemiluminescent reagent (such as CDP-Star, CSPD, and perhaps also enhancer if necessary) is added to the well at a concentration specified by the manufacturer and the slide is covered with a cover slip and sealed with glue.

8) The substrate is assembled on the flat-panel imager for exposure.

Figure 2:
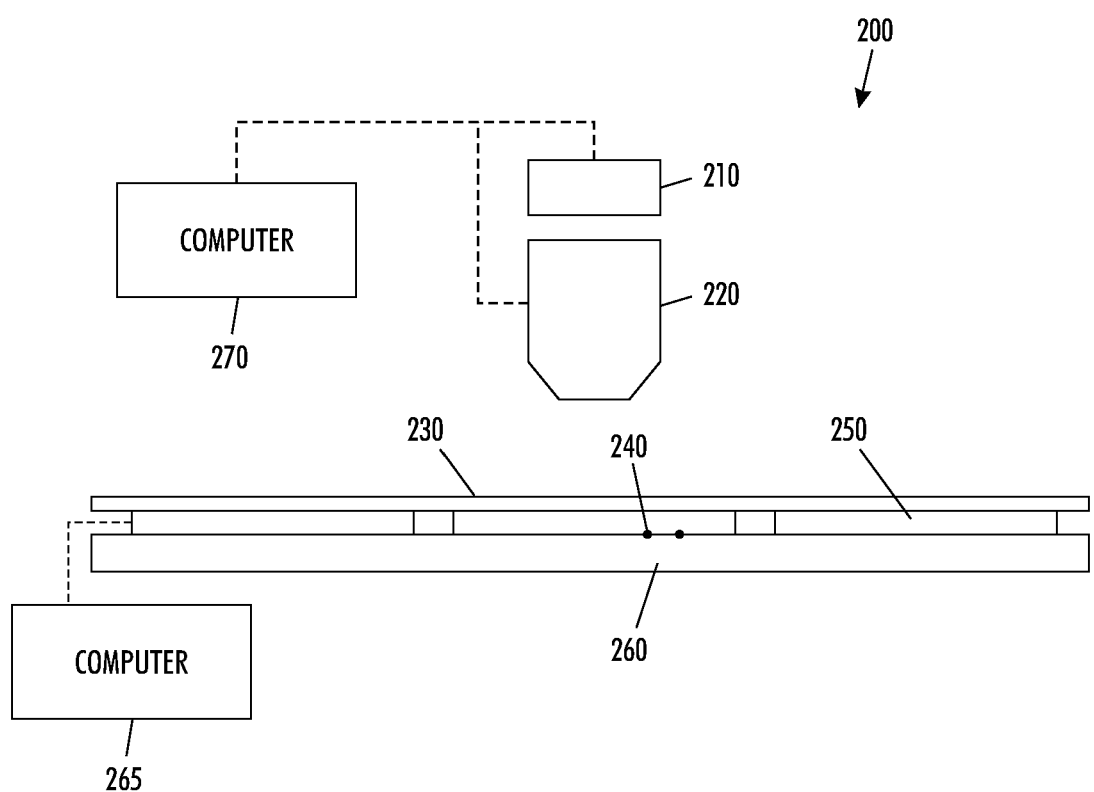
FIG. 2 is a schematic illustration of a system in accordance with the exemplary embodiment.

An exemplary embodiment system 200 is shown in FIG. 2. A conventional microscopic slide or slide assembly 250 on which tagged cells 240 are attached is aligned with a flat-panel imager 260 with the sample side facing the imager. The flat-panel imager 260 includes a data processing device 265, such as a computer or the like. If desired, a removable mirror 230 can be disposed on top of the slide or slide assembly to reflect the photons emitted away from the imager back towards the imager to increase the efficiency of detection. The pixel coordinates of the "potential hits" identified by the flat-panel imager are recorded and translated into spatial data that can be subsequently used by a microscope 220 and camera 210 with computer-controlled movement 270 to accurately image those pixels in high resolution. While it is envisioned that the microscope and camera will be moved during the high-resolution imaging phase, in an alternative embodiment the microscope and camera remain fixed in place and the microscope stage is moved instead; or both of them can move simultaneously. It is also envisioned that the microscope and camera are moved automatically, but in an alternative embodiment a human operator can move and/or control the microscope and camera.

Figure 3:
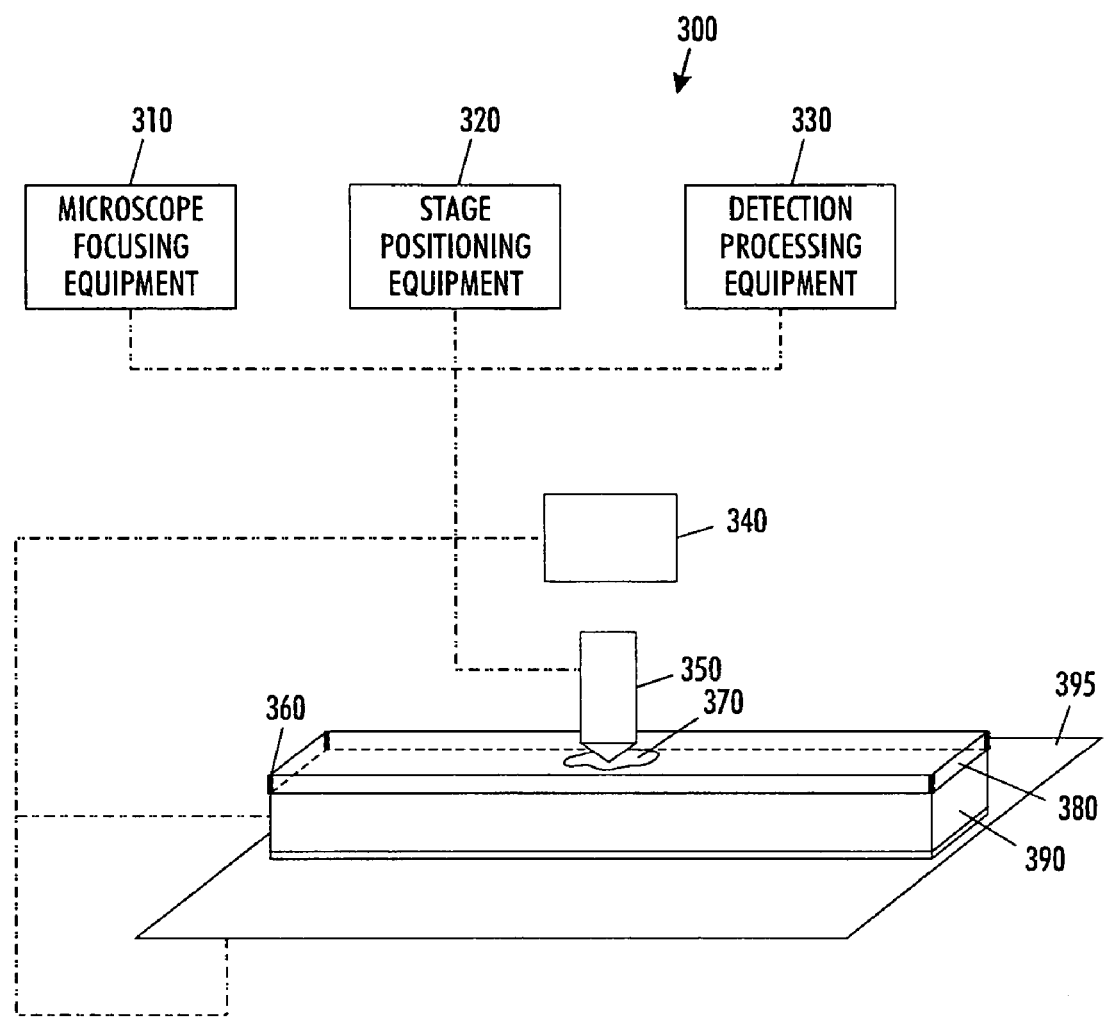
FIG. 3 is a schematic of another system in accordance with the exemplary embodiment.

FIG. 3 shows another exemplary embodiment system 300. Here, an imager 390 is configured in the form of a wellplate. A slide 380 on which tagged cells 370 are attached or otherwise deposited is disposed on the imager 390 with the assistance of an alignment system 360. Because of the alignment system 360, there is no need for optical alignment. In this exemplary embodiment, the alignment system 360 is depicted as four corner posts which define how the slide should be positioned with respect to the imager 390. However, the alignment system can take other forms, either mechanical forms where the slide is positioned to a known position with regards to the imager, or electronic forms where a computer can be used to translate a relative position into an absolute coordinate system. The imager/slide assembly is placed on a wellplate holder on a stage 395 of a microscope. While the microscope stage and flat-panel imager are described and depicted here as two separate systems, in an alternative embodiment the imager serves as the microscope stage and they are an integrated one-piece assembly. Immediately after the potential hits are logged by the imager, high resolution images are acquired by a 40× objective microscope 350 and a sensitive CCD camera 340 with low noise that allows long exposure if necessary. 40× is only an example, as the exemplary embodiment includes the use of microscopes having a objective magnification of from about 10× to about 100×, and particularly about 20× to about 63×. In cases where imager and CCD operate simultaneously, a long working distance objective can be used which allow exposure through the transparent substrate. Detection processing equipment 330 directly translates the "potential hit" coordinates identified by the imager into data that cause stage positioning equipment 320 to move the stage so the "potential hit" is located under the high-resolution microscope. Microscope focusing equipment 310 can move the stage in Z-direction so the "potential hit" is in the focal plane of the high-resolution microscope. Generally, the resolution of the camera is greater than the resolution of the imager, however the exemplary embodiment includes alternate configurations.

In both of the systems 200 and 300, depicted in FIGS. 2 and 3, the operation and/or processing is generally performed in a darkened environment. This can be accomplished by the use of a dark box or placing the system in a dark room. The reason for this is that a darkened environment excludes or at least significantly reduces any external photons.

In another exemplary embodiment, the high-resolution imaging device can begin acquiring a high-resolution image while the flat-panel imager continues to identify "potential hits."

In yet another exemplary embodiment, multiple substrates can be placed simultaneously on the flat-panel imager to be imaged in parallel. It is envisioned that 100-200 $cm^2$ is required to image a typical patient's sample. At currently demonstrated substrate dimensions for TFTs of 30 cm by 40 cm, 12 substrates for 6-12 patients could be simultaneously processed. These numbers are exemplary and should not be construed as limiting.

In other exemplary embodiments, optional devices are provided to allow for different forms of imaging or for chemical reactions to be performed. For example, pipettes could be utilized. The slide samples would first be inserted into the imager and an image of the background light would be taken. Then reagents would be added through the pipettes to induce CL. The background light could be subtracted from the CL light signal to increase sensitivity. Other equipment could be provided for other forms of microscopy to be performed. For example, visible white light microscopy, phase contrast microscopy, DIC microscopy, and fluorescent microscopy require a light source and/or filters but could provide additional information such as additional markers or morphology regarding the targeted rare cells. In this case, cell sample may be labeled with CL probes as well as fluorescent probes. In certain versions, a system in accordance with the exemplary embodiment can comprise one or more filters in which the filters substantially pass light within a particular range of wave lengths and/or substantially block light outside that range of wave lengths. In addition to or instead of the use of the noted filters, an exemplary embodiment system can comprise one or more light sources in which the light sources emit light within a particular range of wave lengths. Thus, the exemplary embodiment system and methods can detect the monochrome emission of light from tagged samples, or detect multiple colors emitted from tagged samples. One or more filters can be used to selectively absorb or block certain wavelengths of light. Multiple optical filters can be used concurrently to form stacks of filters as known by those skilled in the art. The large area flat panel imagers can be used to detect multiple colors emitted from one or more tagged samples.

Calculations supporting the use of flat-panel imagers with CL are provided herein. Previous experiments using CL detection for HeLa cells containing 10-50 copies of the target DNA reported a mean value of 115 emitted photons/sec/cell and a mean value of 844 emitted photons/sec/cell for CaSki cells containing 400-600 copies of the target DNA. See Musiani et al. In immunocytostaining for rare cells, cellular protein is usually the target instead of DNA. Depending on the particular target protein marker, the number of target proteins per cell varies. Fetal or cancerous cells often contain more than 100 copies of membrane or cytosolic proteins while chimerical cancerous genomic DNA stretches also exist at higher than 100 copies per cell. Calculations assume a value of 1.8 emitted photons/sec/tagged protein and 10 copies of the protein with each cell.

The quantum efficiency of a typical flat-panel imager is approximately 75% at 600 nm. The wavelength of the maximum quantum efficiency can be engineered to match the wavelength of emitted photon from CL reagent, which is typically between 400 and 700 nm for most commonly used CL reagents such as Luminol, CSPD or CDP-Star.

The noise performance of a typical, commercially available flat-panel imager (with detector area 20 cm by 24 cm and 127 μm by 127 μm square pixel) can be expressed as:

$$\sigma_{total} = \sqrt{\sigma_{ADC}^2 + \sigma_{line}^2 + \sigma_{pixel}^2} = \sqrt{(1069500) + \frac{(4.5 \times 10^{-15} \times t)}{1.6 \times 10^{-19}}} \, (e_{RMS})$$

where t is the integration time for each frame of digital image. The total noise of the flat-panel imager is dominated by electronic read out noise for short frame times. For long integration times, the noise increases as a function of the square root of integration time because of the shot noise component of the detector dark current.

Figure 4:
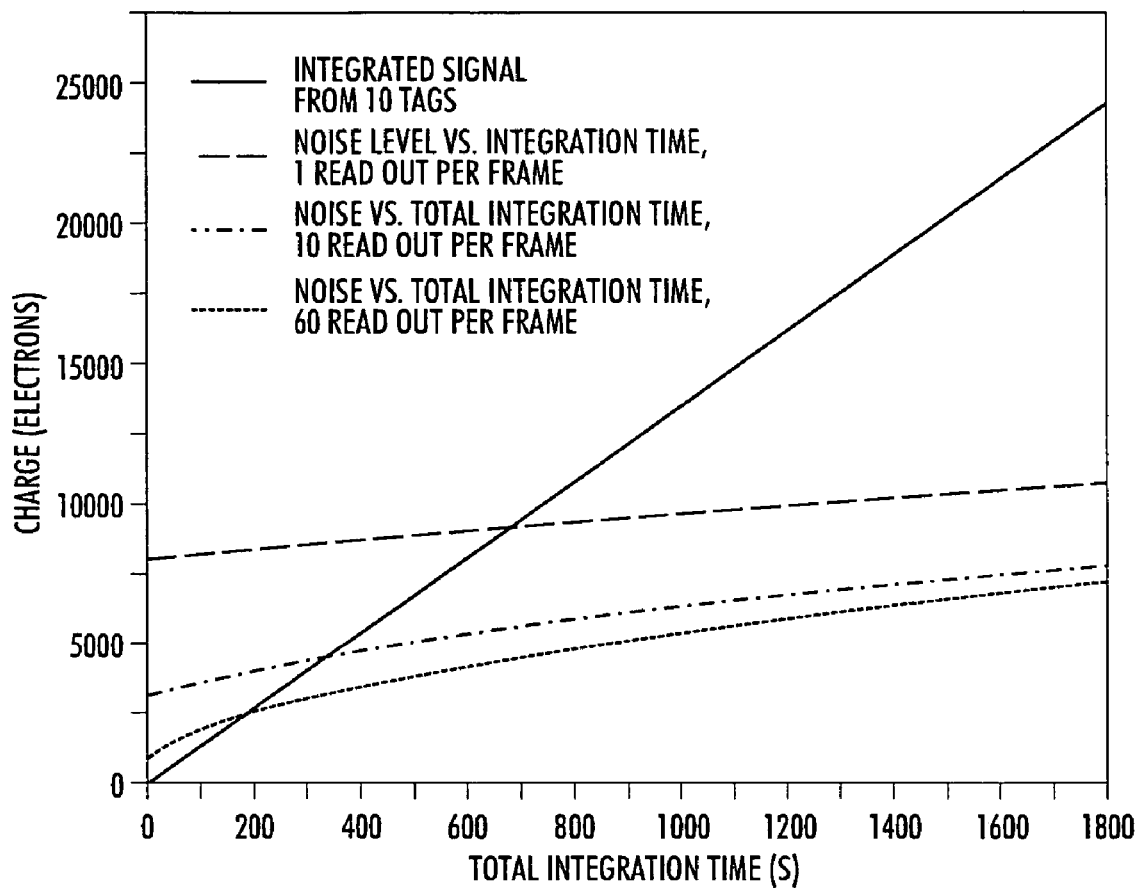
FIG. 4 is a graph showing the number of electrons detected versus the total integration time for three different frame read outs in an exemplary embodiment system.
Figure 5:
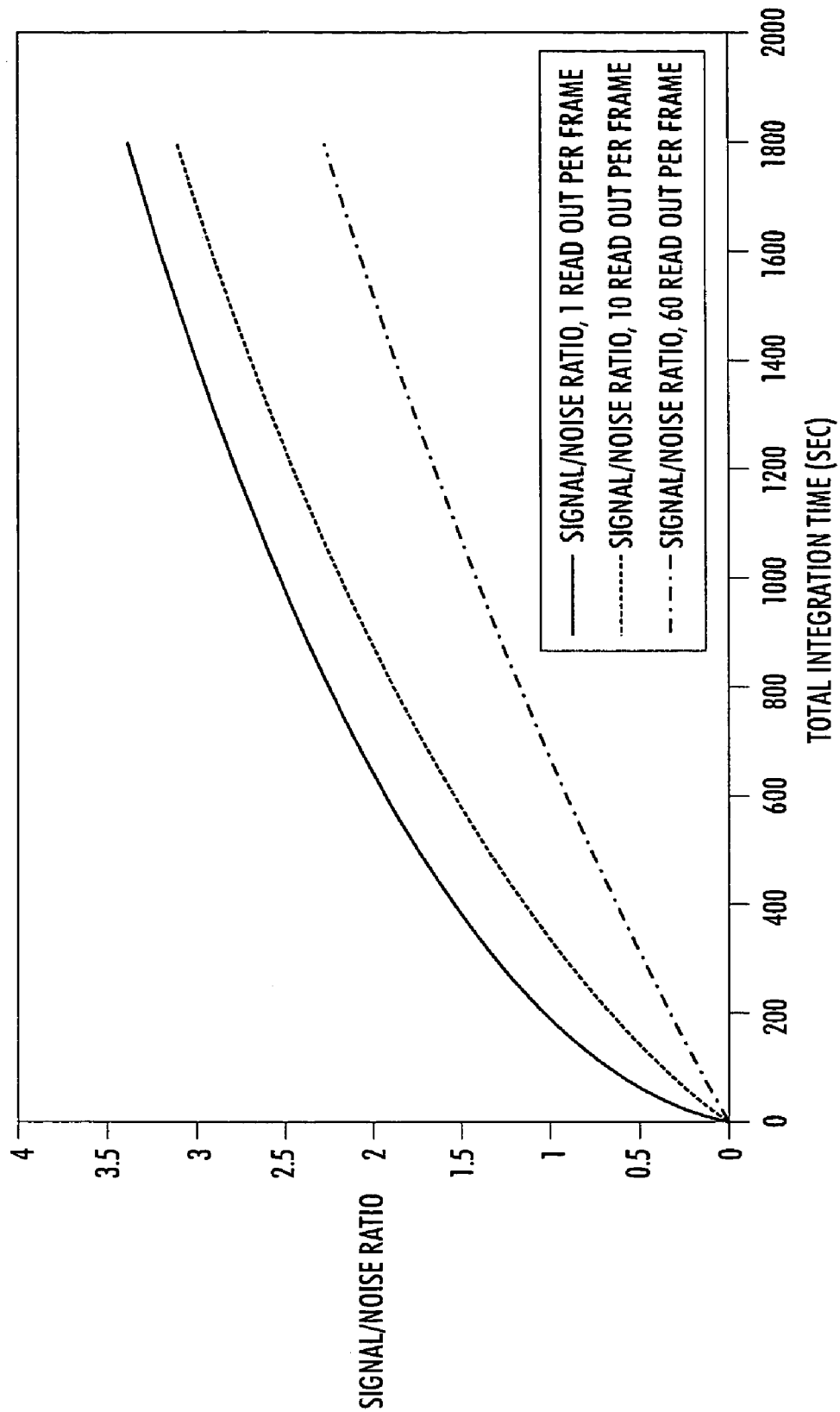
FIG. 5 is a graph showing the signal-to-noise ratio versus total integration time for three different frame read outs in an exemplary embodiment system.

The integrated signal as a function of integration time can be estimated as S=0.75×1.8×10×t, where 0.75 is the quantum efficiency, 1.8 is the fluence of the CL reagent, and 10 is the number of tags attached to the target cell. FIG. 4 shows the comparison of the integrated signal and noise versus integration time. It clearly shows that integrated signal is larger than the noise for integration time t>180 seconds (3 min). To achieve S/N=3, however, requires t>1426 seconds. For flat-panel imagers, constant dark current will saturate the photosensor signal if the frame time is set to such a relatively long period. The solution to this saturation problem is to break the long integration time into n read out frames with frame time t/n and to add the n read out images digitally. The noise power of individual frames is added together such that the total noise can be expressed as:

$$\sigma_{total} = \sqrt{\left[(1069500) + \left[\frac{(4.5 \times 10^{-15} \times t)}{(1.6 \times 10^{-19} \times n)}\right]\right] \times n}$$

where t is the total integration time and n is the number of read outs during the entire exposure process. The curves in FIG. 4 show the total noise for 1, 10, and 60 read out frames respectively and FIG. 5 shows the signal-to-noise ratio versus time for 1, 10, and 60 read out frames. For 10 read out frames, it is possible to achieve S/N>3 at 30 min, or a frame time of 180 seconds. For 1.8 fA dark current and 0.7 pF sensor capacitance, the constant dark current will generate 0.46 V voltage shift on the sensor electrodes, which is well within the dynamic range of typical PIN photo sensors.

At actual frequencies, the number of photons emitted is 10-fold higher than used for the calculation above, resulting in 1 0-fold shorter integration times, or 3 min only. The number of signaling molecules can also be amplified with an additional layer of antibody during sample preparation without proportionally increasing the noise. This would also reduce the integration time required for imaging. Direct X-ray photon detection has been demonstrated to show the capability of single-photon detection. Therefore, a high sensitivity can also be expected for radioisotope tags. Flat-panel imagers with pixel level pre-amplifiers have also been successfully demonstrated.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A one-piece system for detecting the presence of tagged biological agents in a sample, the system comprising:
a large area imager having an image forming surface, the imager being able to form digital or electronic images of the sample free from intermediate image forming lenses, the large area imager further including:
a computer configured to integrate a time period (t), and a (n) number of read-out frames with a frame time t/n, wherein the images are formed by integrating the images over the integrating time period (t), the large area imager configured to break the image integrating time period (t) into the (n) number of read-out frames to avoid noise saturation of the images;
a selectively positionable microscope and camera in viewing relation with the image forming surface; the camera is adapted to acquire an image through the microscope in the form of digital data; and the system or the imaging area is enclosed in a darkened environment to exclude any external photons;
an electronic controller in communication with the imager, microscope, and camera, and configured to position at least one of the imager, microscope, and camera relative to each other in order to image selected regions of the image forming surface.

2. The system of claim 1, wherein the image forming surface comprises a flat panel including a two dimensional array of photosensing devices.

3. The system of claim 2 wherein the flat panel includes thin film transistors.

4. The system of claim 1, wherein the microscope and the imager are integral in relation to each other.

5. The system of claim 1, wherein the microscope contains an objective lens of magnification power of from about 10 to about 100.

6. The system of claim 1, wherein the resolution of the camera is greater than the resolution of the imager.

7. The system of claim 1, wherein the system further comprises one or more filters, the filters substantially passing light within a range of wavelengths and substantially blocking light outside the range of wavelengths.

8. The system of claim 1, wherein the system further comprises one or more light sources, the light sources emitting light within a range of wavelengths.

9. The system of claim 1 further comprising:
a sample receiving substrate disposed on the imager.

10. The system of claim 9 wherein the sample receiving surface includes a coating that facilitates binding of cells thereto.

11. The system of claim 10 wherein the coating is compatible with chemiluminescent detection.

12. The system of claim 1 further comprising:
a component for facilitating detection and/or generation of chemiluminescence.

13. The system of claim 1 further comprising:
positioning equipment for selectively positioning the microscope and the camera based upon the position of the imager.

14. The system of claim 1 further comprising:
positioning equipment for selectively positioning the imager based upon the position of the microscope.

15. The system of claim 1, wherein a wavelength of a maximum quantum efficiency of the large area imager matches a wavelength of an emitted photon from a chemiluminescent reagent in the sample.

16. The system of claim 1, wherein the signal-to-noise ratio (S/N) of the system is at least S/N=3.

17. The system of claim 1, wherein a quantum efficiency of the large area imager is designed to match a wavelength of photons emitted from a selected reagent in the sample which are emitted at a rate of between about 400 to about 700 nm.

18. The system of claim 1, wherein the large area imager is in the form of a wellplate.

19. The system of claim 1, wherein the noise of individual frames is added together such that the total noise can be expressed by a calculation:

$$\sigma_{total} = \sqrt{\left[(1069500) + \left[\frac{(4.5 \times 10^{-15} \times t)}{(1.6 \times 10^{-19} \times n)}\right]\right] \times n},$$

where t is the total integration time and n is the number of readouts during the entire exposure process 20. The system of claim 19, wherein as a frequency of the system increases, a number of photons emitted increases compared to the photons used in the calculation, resulting in shorter integration times.

21. The system of claim 20, wherein the number of photons emitted is tenfold higher than used in the calculation, resulting in tenfold shorter integration times.

22. A one-piece system for detecting the presence of tagged biological agents in a sample, the system comprising:
a large area imager having an image forming surface, the imager being able to form digital or electronic images of the sample free from intermediate image forming lenses;
a selectively positionable microscope and camera in viewing relation with the image forming surface; the camera is adapted to acquire an image through the microscope in the form of digital data; and the system or the imaging area is enclosed in a darkened environment to exclude any external photons; and
a computer in communication with the imager, microscope, and camera, and configured to position at least one of the imager, microscope, and camera relative to each other in order to image selected regions of the image forming surface and integrate a time period (t), and a (n) number of read-out frames with a frame time t/n, wherein the images are formed by integrating the images over the integrating time period (t), the large area imager configured to break the image integrating time period (t) into the (n) number of read-out frames to avoid noise saturation of the images.

23. A one-piece system for detecting the presence of tagged biological agents in a sample, the system comprising:
a large area imager having an image forming surface, the imager being able to form digital or electronic images of the sample free from intermediate image forming lenses,
a computer configured to integrate a time period (t), and a (n) number of read-out frames with a frame time t/n;
a image generator adapted to form the images by integrating the images over the integrating time period (t), the large area imager configured to break the image integrating time period (t) into the (n) number of read-out frames to avoid noise saturation of the images;
a selectively positionable microscope and camera in viewing relation with the image forming surface; the camera is adapted to acquire an image through the microscope in the form of digital data; and the system or the imaging area is enclosed in a darkened environment to exclude any external photons; and
an alignment system in communication with the imager, microscope, and camera, and configured to position at least one of the imager, microscope, and camera relative to each other in order to image selected regions of the image forming surface.

* * * * *